(12) United States Patent
Diehl et al.

(10) Patent No.: US 9,328,039 B2
(45) Date of Patent: *May 3, 2016

(54) PROCESS FOR SELECTIVE HYDROGENATION IN THE PRESENCE OF A CATALYST BASED ON A METAL FROM GROUP VIII PREPARED USING AT LEAST ONE CYCLIC OLIGOSACCHARIDE

(75) Inventors: Fabrice Diehl, Lyons (FR); Anne Claire Dubreuil, Lyons (FR); Josselin Janvier, Nanterre (FR); Cecile Thomazeau, Lyons (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 521 days.

This patent is subject to a terminal disclaimer.

(21) Appl. No.: 13/812,707

(22) PCT Filed: Jun. 24, 2011

(86) PCT No.: PCT/FR2011/000370
§ 371 (c)(1),
(2), (4) Date: Feb. 20, 2013

(87) PCT Pub. No.: WO2012/022851
PCT Pub. Date: Feb. 23, 2012

(65) Prior Publication Data
US 2013/0150639 A1    Jun. 13, 2013

(30) Foreign Application Priority Data
Jul. 29, 2010   (FR) ...................................... 10 03189

(51) Int. Cl.
| | |
|---|---|
| C10G 45/36 | (2006.01) |
| C10G 45/34 | (2006.01) |
| B01J 23/755 | (2006.01) |
| C07C 5/02 | (2006.01) |
| B01J 33/00 | (2006.01) |
| B01J 37/02 | (2006.01) |
| B01J 37/20 | (2006.01) |
| C07C 7/167 | (2006.01) |
| C10G 45/52 | (2006.01) |
| C10G 69/06 | (2006.01) |
| C10G 45/32 | (2006.01) |
| B01J 23/70 | (2006.01) |
| B01J 23/75 | (2006.01) |
| B01J 21/04 | (2006.01) |
| B01J 23/40 | (2006.01) |
| B01J 23/74 | (2006.01) |

(52) U.S. Cl.
CPC ................. *C07C 5/02* (2013.01); *B01J 23/755* (2013.01); *B01J 33/00* (2013.01); *B01J 37/0203* (2013.01); *B01J 37/0205* (2013.01); *B01J 37/20* (2013.01); *C07C 7/167* (2013.01); *C10G 45/34* (2013.01); *C10G 45/36* (2013.01); *C10G 45/52* (2013.01); *C10G 69/06* (2013.01); *B01J 21/04* (2013.01); *B01J 23/40* (2013.01); *B01J 23/74* (2013.01); *C07C 2523/755* (2013.01); *C10G 2300/1011* (2013.01); *C10G 2300/301* (2013.01); *C10G 2300/4018* (2013.01); *C10G 2400/20* (2013.01); *C10G 2400/22* (2013.01); *Y02P 20/52* (2015.11)

(58) Field of Classification Search
CPC .............. C07C 5/00; C07C 5/02; B01J 23/70; B01J 23/75; B01J 23/755; C10G 45/32; C10G 45/34; C10G 45/36
See application file for complete search history.

(56) References Cited

U.S. PATENT DOCUMENTS

| | | | |
|---|---|---|---|
| 3,201,471 A * | 8/1965 | Fisher et al. ................... | 564/511 |
| 2004/0030207 A1 | 2/2004 | Ryu et al. | |
| 2010/0324346 A1 | 12/2010 | Dubreuil et al. | |
| 2012/0093703 A1* | 4/2012 | Lewis et al. ................. | 423/213.2 |
| 2013/0211163 A1* | 8/2013 | Diehl et al. ................... | 585/274 |

FOREIGN PATENT DOCUMENTS

| | | |
|---|---|---|
| EP | 2199269 A1 | 6/2010 |
| FR | 2927267 A1 | 8/2009 |

OTHER PUBLICATIONS

Fisher, G.F. (1969). Journal of the Chemial Society D: Chemical Communications, 15, 886a.*
International Search Report of International Application No. PCT/FR2011/000370 (Nov. 17, 2011).

* cited by examiner

*Primary Examiner* — Brian McCaig
(74) *Attorney, Agent, or Firm* — Millen, White, Zelano & Branigan, P.C.

(57) ABSTRACT

Selective hydrogenation of a polyunsaturated hydrocarbon feed containing at least 2 carbon atoms per molecule and having an end point of 250° C. or less, by contacting said feed with a catalyst having an active phase of at least one metal from group VIII deposited on a support formed by at least one oxide, said catalyst being prepared using a process involving at least:
i) contacting said support with at least one solution containing at least one precursor of metal from group VIII;
ii) contacting said support with at least one organic compound formed from at least one cyclic oligosaccharide composed of at least 6 α-(1,4)-bonded glucopyranose subunits;
iii) calcining to obtain metal from group VIII in oxide form;
i) and ii) possibly being carried out separately, in any order, or simultaneously.

14 Claims, No Drawings

PROCESS FOR SELECTIVE HYDROGENATION IN THE PRESENCE OF A CATALYST BASED ON A METAL FROM GROUP VIII PREPARED USING AT LEAST ONE CYCLIC OLIGOSACCHARIDE

FIELD OF THE INVENTION

The present invention relates to the field of processes for the selective hydrogenation of polyunsaturated compounds present in a hydrocarbon feed, especially in C2-C5 steam cracked cuts and steam cracked gasolines. Selective hydrogenation can transform said polyunsaturated compounds present in oil cuts into the corresponding alkenes, avoiding total saturation of said compounds and thus the formation of the corresponding alkanes. As an example, steam cracked gasolines contain compounds that generate gums, especially diolefins and alkenylaromatics, mixed with mono-olefinic compounds and aromatic compounds in particular. In order to be able to upgrade steam cracked gasolines, they have to be freed of their diolefins or alkenylaromatics contents, the diolefins being selectively hydrogenated to mono-olefins and the alkenylaromatics being selectively hydrogenated to aromatics. More precisely, the present invention relates to a novel process for the selective hydrogenation of polyunsaturated hydrocarbons carried out using a catalyst based on a metal from group VIII and prepared in the presence of at least one cyclic oligosaccharide.

PRIOR ART

Selective hydrogenation catalysts are generally based on metals from group VIII of the periodic classification of the elements, preferably palladium or nickel. The metal is in the form of nanometric metallic particles deposited on a support which may be a refractory oxide in the form of beads, extrudates, trilobes or in forms having other geometries. The quantity of metal from group VIII, the possible presence of a second metallic element, the size of the metal particles and the distribution of the active phase in the support are parameters which are important as regards the performances of the catalysts.

In order to obtain better catalytic performances, especially better selectivity, the use of organic additives in the preparation of metallic selective hydrogenation catalysts has already been disclosed. As an example, patent application EP 0 438 288 teaches the use of reducing organometallic compounds such as triethyl aluminium in a solution containing the precursor Ni(II) (Ni octoate). U.S. Pat. No. 3,642,658 discloses the use of organophosphorus compounds.

SUMMARY OF THE INVENTION

The present invention concerns a process for the selective hydrogenation of a polyunsaturated hydrocarbon feed containing at least 2 carbon atoms per molecule and having an end point of 250° C. or less, said process consisting of bringing said feed into contact with at least one catalyst the active phase of which comprises at least one metal from group VIII deposited on a support formed by at least one oxide, said catalyst being prepared using a process comprising at least:
i) at least one step for bringing at least said support into contact with at least one solution containing at least one precursor of at least said metal from group VIII;
ii) at least one step for bringing at least said support into contact with at least one organic compound formed from at least one cyclic oligosaccharide composed of at least $6\alpha$-(1,4)-bonded glucopyranose subunits;
iii) at least one calcining step to obtain at least said metal from said group VIII in the oxide form;
the steps i) and ii) possibly being carried out separately, in any order, or simultaneously.

In accordance with the selective hydrogenation process of the invention, said metal from group VIII present in the active phase of the catalyst is preferably nickel. In accordance with the selective hydrogenation process of the invention, said catalyst is preferably prepared in the presence of a cyclodextrin as the organic compound.

Surprisingly, it has been discovered that a catalyst the active phase of which comprises at least one metal from group VIII, particularly nickel, and prepared in the presence of at least one organic compound formed from at least one cyclic oligosaccharide composed of at least $6\alpha$-(1,4)-bonded glucopyranose subunits, preferably a cyclodextrin, when used in a selective hydrogenation process, has improved catalytic performances in terms of catalytic activity. This results in better conversion of the feed under identical operating conditions.

DESCRIPTION OF THE INVENTION

The present invention concerns a process for the selective hydrogenation of a polyunsaturated hydrocarbon feed containing at least 2 carbon atoms per molecule and having an end point of 250° C. or less, said process consisting of bringing said feed into contact with at least one catalyst the active phase of which comprises at least one metal from group VIII deposited on a support formed by at least one oxide, said catalyst being prepared using a process comprising at least:
i) at least one step for bringing at least said support into contact with at least one solution containing at least one precursor of at least said metal from group VIII;
ii) at least one step for bringing at least said support into contact with at least one organic compound formed from at least one cyclic oligosaccharide composed of at least $6\alpha$-(1,4)-bonded glucopyranose subunits;
iii) at least one calcining step to obtain at least said metal from said group VIII in the oxide form;
the steps i) and ii) possibly being carried out separately, in any order, or simultaneously.

The feed of polyunsaturated hydrocarbons treated in the selective hydrogenation process of the invention is preferably selected from the C2 steam cracked cut, the C3 steam cracked cut, the C4 steam cracked cut, the C5 steam cracked cut and steam cracked gasolines also known as pyrolysis gasoline. All of these steam cracked cuts and gasolines contain at least 2 carbon atoms per molecule and have an end point of 250° C. or less. More precisely, said polyunsaturated hydrocarbons present in said feed treated using the process of the invention are in particular compounds comprising at least one acetylenic function (i.e. at least one triple bond) and/or at least one diene function (i.e. at least two double bonds). In particular, said polyunsaturated hydrocarbon feed may comprise at least one type of compound containing both an acetylene function and one diene function per molecule.

Hydrocarbon conversion processes such as the steam cracking process from which said hydrocarbon feed to be treated using the selective hydrogenation process of the invention is derived are operated at high temperature and produce a wide variety of mono-unsaturated molecules such as ethylene, propylene, straight chain butenes, isobutene, pentenes as well as mono-unsaturated molecules containing up to approximately 15 carbon atoms. At the same time, polyunsaturated compounds containing several double bonds and/or at least one triple bond are formed, in particular acetylene, propadiene and methylacetylene (or propyne), 1,2- and 1,3-butadiene, butyne, vinylacetylene and ethylacetylene, pentadiene as well as other polyunsaturated compounds present in steam cracked gasolines, in particular styrene and indene compounds.

The C2 steam cracked cut advantageously used to carry out the selective hydrogenation process of the invention has the following composition, for example: 90% by weight of ethylene, of the order of 0.3% to 2% by weight of acetylene, the remainder essentially being ethane. In certain C2 steam cracked cuts, between 0.1% and 1% by weight of C3 compounds may also be present. The specifications concerning the concentrations of polyunsaturated compounds, in particular acetylene, in the steam cracking C2 cut hydrogenated using the process of the invention are very low, namely from 0.1 to 5 ppm by weight depending on the envisaged application.

The C3 steam cracked cut advantageously used to carry out the selective hydrogenation process of the invention has the following mean composition, for example: of the order of 90% by weight of propylene, of the order of 3% to 8% by weight of propadiene and methylacetylene, the remainder essentially being propane. In certain C3 cuts, between 0.1% and 2% by weight of C2 compounds and of C4 compounds may also be present. The specifications concerning the concentrations of these polyunsaturated compounds, in particular propadiene and methylacetylene, in the C3 steam cracked cut hydrogenated using the process of the invention to upgrade it in petrochemical and polymerization units are very low, namely 20-30 ppm by weight of MAPD (methylacetylene and propadiene) for chemical quality propylene (upgrading of C3 steam cracked cut hydrogenated in petrochemicals units) and less than 10 ppm by weight or even less than 1 ppm by weight for the "polymerization" quality (upgrading C3 steam cracked cut hydrogenated in polymerization units).

The C4 steam cracked cut advantageously used to carry out the selective hydrogenation process of the invention has the following mean composition by weight, for example: 1% by weight of butane, 46.5% by weight of butene, 51% by weight of butadiene, 1.3% by weight of vinylacetylene (VAC) and 0.2% by weight of butyne. In certain C4 cuts, between 0.1% and 2% by weight of C3 compounds and C5 compounds may also be present. The specifications concerning the concentrations of these polyunsaturated compounds, in particular butadiene, vinylacetylene and butyne, in the C4 steam cracked cut hydrogenated using the process of the invention are severe, namely a diolefins content strictly less than 10 ppm by weight for an upgraded C4 cut for petrochemicals or polymerization.

The C5 steam cracked cut advantageously used to carry out the selective hydrogenation process of the invention has, for example, the following composition: 21% by weight of pentanes, 45% by weight of pentenes, 34% by weight of pentadienes.

The steam cracked gasoline or pyrolysis gasoline advantageously used to carry out the selective hydrogenation process of the invention corresponds to a hydrocarbon cut with a boiling point generally in the range 0° C. to 250° C., preferably in the range 10° C. to 220° C. The polyunsaturated hydrocarbons present in said steam cracked gasoline are in particular diolefinic compounds (butadiene, isoprene, cyclopentadiene), styrene compounds (styrene, alpha-methylstyrene) and indene compounds (indene). The steam cracked gasoline also generally comprises the C5-C12 cut with traces of C3, C4, C13, C14, C15 (for example between 0.1% and 3% by weight for each of these cuts). As an example, the steam cracked gasoline may advantageously have the following distribution, depending on the chemical functions present in the compounds of the hydrocarbon feed (as a % by weight):

Paraffins+naphthenes: 10-25
Aromatics: 50-70
Mono-olefins: 5-20
Diolefins: 10-25
Alkenyl aromatics (for example styrene): 2-10
Sulphur: 5-500 ppm Preferably, the polyunsaturated hydrocarbon feed treated in accordance with the selective hydrogenation process of the invention is a steam cracked gasoline.

The selective hydrogenation process of the invention is aimed at eliminating said polyunsaturated hydrocarbons present in said feed to be hydrogenated by carrying out conversion of said polyunsaturated hydrocarbons into the corresponding alkenes and avoiding total saturation of said hydrocarbons in order to avoid the formation of the corresponding alkanes. As an example, when said feed is a steam cracked gasoline, the selective hydrogenation process of the invention is aimed at selectively hydrogenating said polyunsaturated hydrocarbons present in said feed to be treated such that the diolefinic compounds are partially hydrogenated into mono-olefins and the styrene and indene compounds are partially hydrogenated into the corresponding aromatic compounds.

The selective hydrogenation process technology of the invention involves, for example, the use of injection technology, in riser or dropper mode, of the polyunsaturated hydrocarbon feed and hydrogen in at least one fixed bed reactor. Said reactor may be of the isothermal or adiabatic type. An adiabatic reactor is preferred. The polyunsaturated hydrocarbon feed may advantageously be diluted by one or more re-injection(s) of effluent derived from said reactor where the selective hydrogenation reaction is carried out, at various points of the reactor, located between the inlet and outlet of the reactor. The selective hydrogenation process technology of the invention may also advantageously involve implanting at least said supported catalyst in a reactive distillation column or in exchanger-reactors. The hydrogen stream may be introduced at the same time as the feed to be hydrogenated and/or at a different point in the reactor.

Depending on the nature of the feeds to be hydrogenated, the selective hydrogenation process of the invention is carried out either in the liquid phase or in the gas phase. In the case in which the feed to be treated is a C2 steam cracked cut, the selective hydrogenation of the invention is carried out in the gas phase, at a total pressure generally in the range 1 to 5 MPa, a temperature in the range 20° C. to 250° C., preferably in the range 35° C. to 150° C., a molar ratio of hydrogen/(polyunsaturated hydrocarbons to be hydrogenated) in the range 0.8 to 200, preferably in the range 0.9 to 120. The hourly space velocity (defined as the ratio of the volume flow rate of feed to the volume of catalyst) is in the range 1000 to 20000 $h^{-1}$, preferably in the range 4000 to 12000 $h^{-1}$.

In the case in which the feed is a C3 steam cracked cut, a C4 steam cracked cut, a C5 steam cracked cut or a steam cracked gasoline, the selective hydrogenation process of the invention is carried out in the liquid phase under the following operating conditions: a total pressure in the range 0.4 to 5 MPa, a temperature in the range 20° C. to 200° C. and a molar ratio of hydrogen/(polyunsaturated hydrocarbons to be hydrogenated) in the range 0.1 to 4, preferably in the range 1 to 2. The hourly space velocity (defined as the ratio of the volume flow rate of feed to the volume of catalyst) established under these conditions is generally in the range 0.2 to 100 $h^{-1}$, preferably in the range 5 to 80 $h^{-1}$ and more preferably in the range 10 to 50 $h^{-1}$.

In accordance with a preferred implementation of the process of the invention in which the polyunsaturated hydrocarbon feed is a steam cracking gas, the selective hydrogenation is carried out under pressure, in the liquid phase, in the presence of a quantity of hydrogen which is in slight excess with respect to the stoichiometric value for selective hydrogenation of the polyunsaturated hydrocarbons present in the feed, i.e. an excess which is advantageously in the range 5% to 30%. For selective hydrogenation of a steam cracked gasoline, the process of the invention is carried out at a temperature in the range 20° C. to 200° C., at a total pressure which is generally sufficient to maintain at least 80% of the feed to be treated in the liquid phase at the inlet to the reaction unit. Said pressure is preferably in the range 0.4 to 5 MPa, more preferably in the range 1 to 4 MPa. The hourly space velocity (defined as the ratio of the volume flow rate of the feed to the volume of catalyst) established under these conditions is generally in the range 0.2 to 30 $h^{-1}$, preferably in the range 1 to 20 $h^{-1}$ and more preferably in the range 2 to 10 $h^{-1}$.

The catalyst employed to carry out the selective hydrogenation process of the invention comprises an active metallic phase deposited on a support, said active phase comprising at least one metal from group VIII of the periodic classification of the elements, preferably selected from palladium and nickel; highly preferably, said metal from group VIII is nickel. Said metal(s) from group VIII are in the form of nanoparticles deposited on said support. In general, the quantity of metal(s) from group VIII in the catalyst is in the range 0.01% to 50% by weight of the catalyst mass, preferably in the range 0.05% to 30% by weight of the catalyst mass. More precisely, when the active phase comprises palladium, the quantity of palladium in said catalyst is preferably in the range 0.01% to 1% by weight of the catalyst mass, more preferably in the range 0.05% to 0.6% by weight of the catalyst mass. When the active phase comprises nickel, the quantity of nickel in said catalyst is preferably in the range 1% to 50% by weight of the catalyst mass, more preferably in the range 5% to 40% by weight of the catalyst mass and still more preferably in the range 8% to 30% by weight of the catalyst mass. The active phase of said catalyst also advantageously comprises at least one additional metal selected from metals from group VIII and metals from group IB. Preferably, the additional metal from group VIII is selected from palladium, platinum, ruthenium, rhodium and iridium. Preferably, the additional metal from group IB is selected from copper, gold and silver. Said additional metal(s) is (are) preferably present in an amount representing 0.01% to 20% by weight of the catalyst mass, preferably 0.1% to 10% by weight of the catalyst mass and still more preferably 0.1% to 5% by weight of the catalyst mass. Highly preferably, said active phase is free of metals belonging to group VIB (Cr, Mo, W) of the periodic classification of the elements.

The support on which said active phase is deposited is advantageously formed from at least one refractory oxide preferably selected from oxides of metals from groups IIA, IIIB, IVB, IIIA and IVA using the CAS notation of the periodic classification of the elements. Preferably, said support is formed from at least one simple oxide selected from alumina ($Al_2O_3$), silica ($SiO_2$), titanium oxide ($TiO_2$), zirconia ($ZrO_2$), magnesia ($MgO_2$) and thorium oxide. It may also advantageously be formed from a plurality of simple oxides selected from alumina ($Al_2O_3$), silica ($SiO_2$), titanium oxide ($TiO_2$), zirconia ($ZrO_2$), magnesia ($MgO_2$) and thorium oxide. It may also advantageously be formed from a mixture of an oxide selected from alumina ($Al_2O_3$), silica ($SiO_2$), titanium oxide ($TiO_2$), zirconia ($ZrO_2$), magnesia ($MgO_2$) and thorium oxide with other oxides of metals from the periodic classification of the elements. The preferred support is selected from aluminas, silicas and silica-aluminas. Highly preferably, said support is an alumina or a silica and still more preferably, it is an alumina. The pore volume of the support is generally in the range 0.1 $cm^3/g$ to 1.5 $cm^3/g$, preferably in the range 0.5 $cm^3/g$ to 1 $cm^3/g$. The specific surface area of the support is generally in the range 10 $m^2/g$ to 250 $m^2/g$, preferably in the range 30 $m^2/g$ to 200 $m^2/g$ and still more preferably in the range 40 $m^2/g$ to 180 $m^2/g$. Said porous support is advantageously in the form of beads, extrudates, pellets or irregular, non-spherical agglomerates the specific form of which may be the result of a crushing step. Highly advantageously, said support is in the form of beads or extrudates and highly preferably in the form of beads.

The catalyst used in the selective hydrogenation process of the invention is prepared using a process comprising at least:
i) at least one step for bringing at least said support as described above into contact with at least one solution containing at least one precursor of at least said metal from group VIII;
ii) at least one step for bringing at least said support as described above into contact with at least one organic compound formed from at least one cyclic oligosaccharide composed of at least 6α-(1,4)-bonded glucopyranose subunits;
iii) at least one calcining step to obtain at least said metal from said group VIII in the oxide form;
the steps i) and ii) possibly being carried out separately, in any order, or simultaneously.

Deposition of at least said metal from group VIII on said support in accordance with the implementation of said step i) may be carried out using any method which is well known to the skilled person. Said step i) is preferably carried out by impregnation of the support consisting, for example, of bringing said support into contact with at least one solution, aqueous or organic, containing at least one precursor of at least said metal from group VIII, preferably nickel, in the dissolved state, or bringing said support into contact with at least one colloidal solution of at least one precursor of at least said metal from group VIII, preferably nickel, in the oxide form (oxide, oxy(hydroxide) or hydroxide nanoparticles of metal(s) from group VIII) or in the reduced form (metallic nanoparticles where the metal(s) from group VIII is (are) in the reduced state). In particular, said step i) may be carried out by dry impregnation, excess impregnation, or by deposition-precipitation (as described in U.S. Pat. No. 5,874,381 and U.S. Pat. No. 6,534,436) using methods which are well known to the skilled person. Preferably, said step i) is carried out by dry impregnation, which consists of bringing the catalyst support into contact with a solution containing at least one precursor of at least said metal from group VIII the volume of which is equal to the pore volume of the support to be impregnated. This solution contains metallic precursors of the metal or metals from group VIII in the desired concentration, in the dissolved form and/or in the form of colloidal nanoparticles in suspension.

In the case of bringing said support into contact with at least one solution, aqueous or organic, containing at least one precursor of at least said metal from group VIII in the dissolved state, said metal(s) from group VIII is (are) brought into contact with said support using any metallic precursor which is soluble in an aqueous phase or an organic phase. When it is introduced in organic solution, said precursor of the metal from group VIII, preferably nickel, is, for example, the oxalate or acetate of said metal from group VIII. Preferably, said precursor of the metal from group VIII is introduced in aqueous solution, for example in the form of a nitrate, carbonate, acetate, chloride or oxalate, complexes formed by a polyacid or an acid-alcohol and its salts, complexes formed with acetylacetonates, or any other inorganic derivative which is soluble in aqueous solution, which is brought into contact with said support. In the preferred case in which said metal from group VIII is nickel, the nickel precursor is advantageously nickel nitrate, nickel chloride or nickel acetate.

Contact of said organic compound used to carry out said step ii) with said support is carried out by impregnation, in particular by dry impregnation or excess impregnation, preferably by dry impregnation. Said organic compound is preferably impregnated onto said support after dissolving into aqueous solution.

Said organic compound is formed from at least one cyclic oligosaccharide composed of at least 6α-(1,4)-bonded glucopyranose subunits. A spatial representation of a glucopyranose subunit is given below:

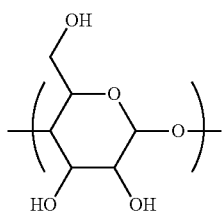

Said organic compound is preferably selected from cyclodextrins, substituted cyclodextrins, polymerized cyclodextrins and mixtures of cyclodextrins. Cyclodextrins are a family of cyclic oligosaccharides composed of α-(1,4)-bonded glucopyranose subunits. They are cage molecules. In accordance with the invention, preferred cyclodextrins are α-cyclodextrin, β-cyclodextrin and γ-cyclodextrin respectively composed of 6, 7 and 8α-(1,4)-bonded glucopyranose subunits. Developed representations of α-cyclodextrin, β-cyclodextrin and γ-cyclodextrin are given below. Preferably, to carry out said step ii), β-cyclodextrin is used, composed of 7α-(1,4)-bonded glucopyranose subunits. Cyclodextrins are commercially available compounds.

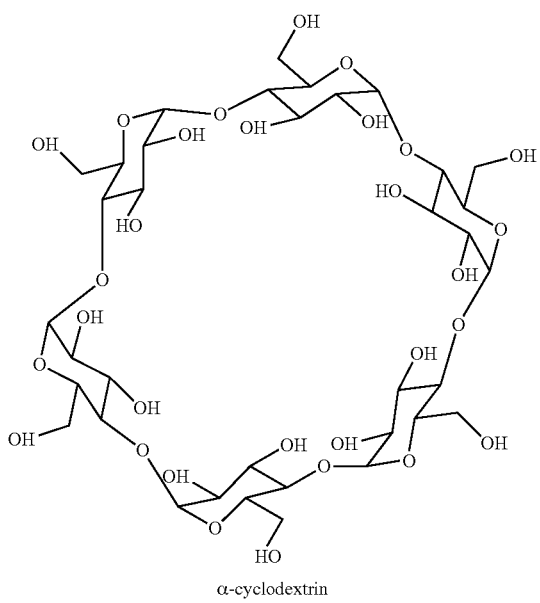

α-cyclodextrin

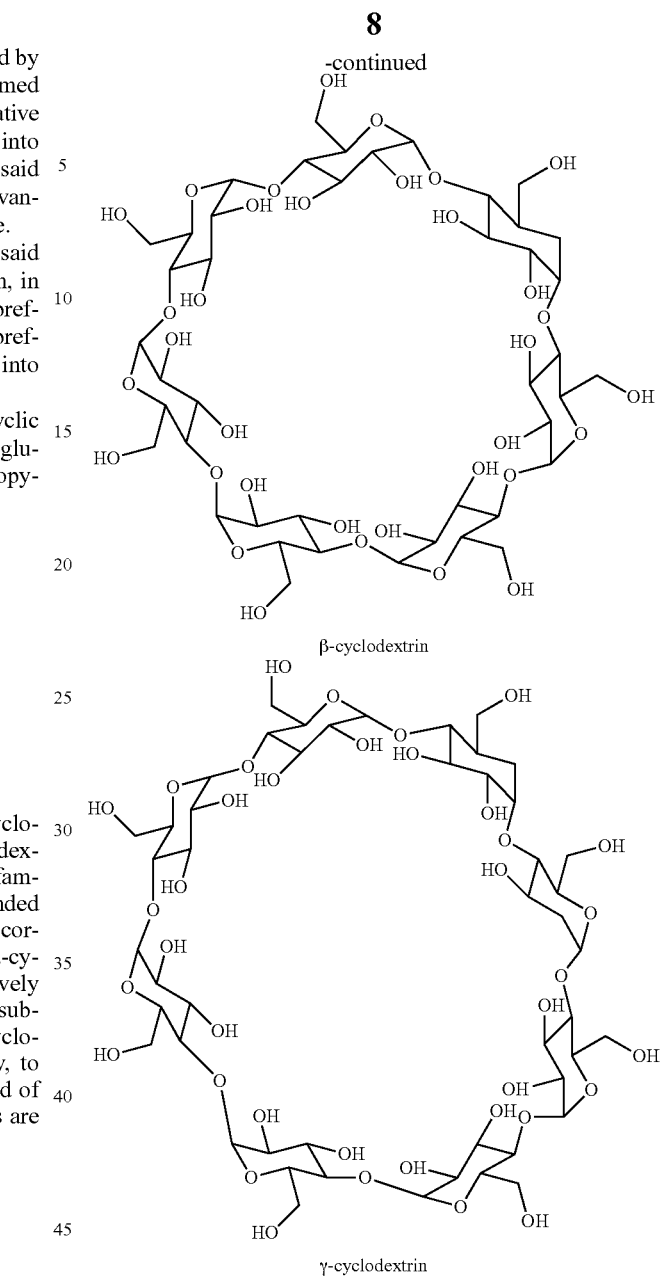

β-cyclodextrin

γ-cyclodextrin

The substituted cyclodextrins advantageously employed to carry out said step ii) are constituted by 6, 7 or 8α-(1,4)-bonded glucopyranose subunits, wherein at least one is mono- or polysubstituted. The substituents may be attached to one or more hydroxyl group(s) present in the molecule, namely to hydroxyl groups bonded directly to the cycle of a glucopyranose unit and/or to the hydroxyl bonded to the $CH_2$ group itself bonded to the cycle of a glucopyranose unit. More preferably, said substituted cyclodextrins carry one or more substituents, which may be identical or different, selected from saturated or unsaturated alkyl radicals, which may or may not be functionalized, and ester, carbonyl, carboxyl, carboxylate, phosphate, ether, polyether, urea, amide, amine, triazole or ammonium functions. Preferred substituted cyclodextrins are methylated, ethylated, propylated and allyl (i.e. having a function with the semi-developed formula —$CH_2$—$CH=CH_2$) cyclodextrins, succinylated (i.e. having a function with the semi-developed formula R—OCO—$CH_2$—$CH_2COOH$) cyclodextrins, carboxylated, carboxymethylated, acetylated, 2-hydroxypropylated and polyoxyethylenated cyclodextrins. The cyclodextrin mono- or poly-substituent groups may also be a monosaccharide or disaccharide molecule such as a molecule of maltose, glucose, fructose or saccharose.

Particularly advantageous substituted cyclodextrins for carrying out said step ii) are hydroxypropyl beta-cyclodextrin and methylated beta-cyclodextrins.

The polymerized cyclodextrins which are advantageously employed for carrying out said step ii) are polymers wherein the monomers are each constituted by a cyclic oligosaccharide composed of 6, 7 or 8α-(1,4)-bonded glucopyranose subunits, which may or may not be substituted. A cyclodextrin in the polymerized form, cross-linked or not, which may advantageously be used to carry out said step ii) is, for example, of the type obtained by polymerization of monomers of beta-cyclodextrin with epichlorhydrin or a polyacid.

Advantageous mixtures of cyclodextrins employed in carrying out said step ii) employ substituted or unsubstituted cyclodextrin. Said mixtures could, for example, contain each of the three types of cyclodextrins (alpha, beta and gamma) jointly and in varying proportions.

Introduction of said organic compound, preferably a cyclodextrin and highly preferably beta-cyclodextrin, for carrying out said step ii) is such that the molar ratio {(metal(s) from group VIII in the oxide form present in the active phase of the catalyst obtained at the end of said step iii)/organic compound} is in the range 10 to 300, preferably in the range 10 to 180. The metal(s) from group VIII taken into account for the calculation of said molar ratio are the metals introduced to carry out said step i) and optionally any additional metal(s) and are in the oxide form in the active phase of the catalyst obtained from said step iii). As a result, said metal(s) from group VIII present in the active phase of the catalyst obtained at the end of said step iii) can be reduced: it (they) will be reduced prior to using them in the hydrocarbon synthesis process of the invention.

The process for preparing the catalyst used in the selective hydrogenation process of the invention includes several implementations.

A first implementation consists of carrying out said steps i) and ii) simultaneously such that said organic compound, preferably a cyclodextrin, and at least said precursor of at least said metal from group VIII present in the active phase are co-impregnated onto said support in a single step termed a co-impregnation step. Said first implementation advantageously comprises carrying out one or more steps i). In particular, one or more steps i) advantageously precede and/or follow said co-impregnation step. In accordance with said first implementation, each of the steps carried out is preferably followed immediately by at least one step for drying then by at least one calcining step. In particular, said co-impregnation step is followed by at least one drying step then by at least one calcining step. Said first implementation may comprise several co-impregnation steps; steps i) and ii) are carried out simultaneously several times. Said calcining step iii) is at least carried out when all of the steps for depositing at least said metal from group VIII onto the catalyst support have been carried out.

A second implementation consists of carrying out said step i) prior to said step ii). In accordance with said second implementation, one or more steps i) for depositing at least said metal from group VIII present in the active phase of the catalyst precede(s) said step ii). Preferably, each of said steps i) is followed immediately by at least one drying step and by at least one calcining step. In particular, the last step i) is advantageously followed by at least one drying step and by at least one calcining step in accordance with said step iii) before carrying out said step ii). Said step ii) is advantageously followed by at least one drying step and optionally by at least one calcining step.

A third implementation consists of carrying out said step ii) prior to said step i). Said step ii) is preferably followed immediately by at least one drying step and optionally by at least one calcining step before carrying out said step i). Advantageously, said step ii) is followed by several steps i). Preparation of the catalyst in accordance with said third implementation is advantageously terminated by said calcining step iii).

Each of the three implementations described above may be carried out independently such that the catalyst used in the process of the invention is prepared either in accordance with said first implementation or in accordance with said second implementation or in accordance with said third implementation. However, it may be advantageous to associate said first implementation with said second implementation or with said third implementation: thus, both the metal from group VIII present in the active phase and the organic compound, preferably a cyclodextrin, are deposited in at least two events on the catalyst support, namely at least once by co-impregnation and at least once by successive impregnation.

The drying steps carried out to prepare the catalyst prepared in accordance with at least one implementation described above are carried out at a temperature in the range 80° C. to 160° C. They are preferably carried out for a period in the range 1 to 24 hours. Said calcining step iii) is carried out at a temperature in the range 200° C. to 800° C., preferably in the range 250° C. to 600° C. and more preferably in the range 300° C. to 500° C. It is preferably carried out for a period in the range 1 to 6 hours. The calcining steps carried out to prepare the catalyst prepared in accordance with at least one implementation described above are advantageously carried out under the same conditions as said step iii).

The catalyst obtained at the end of said step iii) after carrying out steps i) and ii) in accordance with at least one of the three implementations described above is in the oxide state.

The preparation of the catalyst used in the selective hydrogenation process of the invention advantageously comprises at least one step iv) consisting of depositing at least one additional metal selected from metals from group VIII and metals from group D3 on said catalyst support. The deposition of at least said additional meal on said support may be carried out using any method known to the skilled person, preferably by impregnation of the catalyst support using at least one solution containing at least one precursor of said additional metal, for example by dry impregnation or by excess impregnation. Said step iv) may be carried out either separately from steps i) and ii) in any order, or simultaneously with said step i) and/or said step ii). More precisely, it may be carried out in association with at least one of the three implementations for the preparation of the catalyst described above. Preferably, said step iv) is followed immediately by at least one drying step then by at least one step for calcining under conditions (temperature, duration) such as those described above.

In the preferred case in which the active phase of the catalyst comprises nickel as the metal from group VIII, the preparation of the catalyst used in the selective hydrogenation process of the invention advantageously comprises at least one step v) consisting of passivating said catalyst by at least one sulphur-containing compound. Said step v) is carried out after carrying out steps i), ii) and iii) and optionally iv). In a preferred implementation, said step v) is carried out ex situ, i.e. before loading the catalyst into the reaction unit for the selective hydrogenation process of the invention. Said step v)

is carried out by implementing methods which are known to the skilled person and in particular, for example, by implementing one of the methods described in patent documents EP 0 466 567 (B1), U.S. Pat. No. 5,153,163, FR 2 676 184 and WO 2004/098774. Preferably, said step v) is carried out by bringing the catalyst obtained after carrying out steps i), ii) and iii) and optionally iv) into contact with at least one solution comprising at least one organic reducing agent and at least one sulphur-containing compound. Highly preferably, said step v) is carried out by impregnating the catalyst obtained after carrying out steps i), ii) and iii) and optionally iv) with said solution. The organic reducing agent present in said solution is, for example, selected from formic acid, formaldehyde, acetic acid, ethanol, methanol, ethyl formate and methyl formate. The sulphur-containing compound present in said solution is, for example, a compound with formula OH—R1—S—S—R2—OH (were R1 and R2 may be any type of organic radical) such as di-ethanol-disulphide (DEODS) or an organic polysulphide compound with formula R—S(n)-R' where R and R' are organic radicals and n is in the range 3 to 20, for example dodecylpolysulphide. The quantity of sulphur introduced is such that the catalyst passivated by sulphur comprises 0.2% to 2% by weight of sulphur. The quantity of organic reducing agent is such that the passivated catalyst comprises in the range 100 ppm (parts per million) to 50% by weight of said reducing agent. After introducing said sulphur-containing compound onto the catalyst, said catalyst then undergoes a heat treatment carried out at a temperature in the range 100° C. to 200° C. for a period in the range 30 minutes to 3 hours.

Before carrying out the selective hydrogenation process of the invention, the catalyst prepared using at least one of the three implementations described above, in association or not in association with said step iv) and/or said step v), is at least partially in the oxide form. Said catalyst may be wholly or partially free of said organic compound formed from at least one cyclic oligosaccharide composed of at least 6α-(1,4)-bonded glucopyranose subunits. In the preferred case in which the active phase of the catalyst comprises nickel as the metal from group VIII and said catalyst has been prepared using a process comprising the use of at least said passivation step v), before carrying out the selective hydrogenation process of the invention, said catalyst is advantageously at least partially in the oxide form and/or at least partially in the reduced form and/or at least partially in the sulphide form. Preferably, the quantity of sulphur in said catalyst is less than 2% by weight of the mass of said catalyst.

Prior to using it in the catalytic reactor and carrying out the selective hydrogenation process of the invention, the catalyst undergoes at least one reducing treatment, for example with hydrogen, pure or diluted, at high temperature. This treatment means that said catalyst can be activated and form particles of metal, in particular metal from group VIII, in the zero valency state. This reduction treatment is carried out either in situ (in the same reactor as that in which the selective hydrogenation is carried out) or ex situ before being loaded into the reactor. The temperature of this reduction treatment is preferably in the range 100° C. to 600° C., preferably in the range 150° C. to 450° C., and its duration is in the range 1 to 40 hours, preferably 2 to 20 hours.

When the catalyst comprises nickel as the metal from group VIII in the active phase and when it has not undergone said passivation step v), said reducing treatment is carried out at a temperature in the range 100° C. to 600° C., preferably in the range 200° C. to 500° C., for a period in the range 2 to 40 hours, preferably in the range 5 to 30 hours. The rise in temperature to the desired reduction temperature is generally slow, for example fixed at between 0.1 and 5° C./min. Preferably, said reducing treatment is followed by at least one step for passivation by sulphur carried out in situ, i.e. in the same reactor as that in which the selective hydrogenation reaction is carried out. Said passivation step is carried out by injecting at least one sulphur-containing compound before bringing said catalyst into contact with the polyunsaturated hydrocarbon feed to be hydrogenated in order to obtain a sulphur-passivated catalyst in which the sulphur content is in the range 0.1% to 2% by weight with respect to the catalyst mass. The sulphur-containing compound is, for example, selected from the following compounds: thiophene, thiophane, alkyl monosulphides such as dimethylsulphide, diethylsulphide, dipropylsulphide and propylmethylsulphide.

When the catalyst comprises nickel as the metal from group VIII in the active phase and it has undergone said passivation step v), said reducing treatment is carried out at a temperature in the range 100° C. to 400° C., preferably in the range 150° C. to 350° C., for a period in the range 2 to 40 hours, preferably in the range 5 to 30 hours. The temperature rise to the desired reduction temperature is generally slow, for example fixed at between 0.1 to 5° C./min.

The invention is illustrated in the following examples.

EXAMPLES

The series of catalysts prepared in Examples 1, 2, 3 and 4 were prepared with the same nickel element content. The support used for the preparation of each of these catalysts was the support formed from delta alumina beads with a pore volume of 0.67 ml/g and a BET surface area of 70 m$^2$/g.

Example 1 (Comparative)

Preparation of a Supported Catalyst A with Formula Ni/Al$_2$O$_3$ by Impregnation of Nickel Nitrate An aqueous nickel nitrate solution was prepared at 25° C. by diluting 22.3 g of nickel nitrate Ni(NO$_3$)$_2$, 6H$_2$O in demineralized water to a volume which corresponded to the pore volume of said alumina support. This solution was then impregnated onto 50 g of said alumina support. The solid was then dried in air overnight at 120° C. and calcined in air at 450° C. for 2 hours.

The oxide catalyst A prepared thereby contained 9% by weight of the element nickel supported on alumina.

Example 2 (Invention)

Preparation of a Supported Catalyst B with Formula Ni/Al$_2$O$_3$ by Successive Impregnation of β-Cyclodextrin then Nickel Nitrate An aqueous solution was prepared by dissolving 0.96 g of β-cyclodextrin (SIGMA-ALDRICH, 98% pure) in 50 ml of water. This solution was then dry impregnated onto said alumina support. The solid B1 obtained thereby was dried in air overnight at 120° C. and calcined in air at 450° C. for 2 hours. An aqueous nickel nitrate solution was prepared at 25° C. by diluting 22.3 g of nickel nitrate Ni(NO$_3$)$_2$, 6H$_2$O in demineralized water to a volume which corresponded to the pore volume of the solid B1. This solution was then impregnated onto 50 g of the prepared solid B1. The solid was then dried in air overnight at 120° C. and calcined in air at 450° C. for 2 hours.

The oxide catalyst B prepared thereby contained 9% by weight of the element nickel supported on alumina.

Example 3 (Invention)

Preparation of a Supported Catalyst C with Formula Ni/Al$_2$O$_3$ by Simultaneous Impregnation (Co-Impregnation) of β-Cyclodextrin and Nickel Nitrate An aqueous solution containing 6.3 g of β-cyclodextrin (SIGMA-ALDRICH, 98% pure) and 22.4 g of nickel nitrate Ni(NO$_3$)$_2$, 6H$_2$O in demineralized water was prepared to a volume which corresponded to the pore volume of said alumina support. This solution was then impregnated onto 50 g of said alumina support. The solid obtained thereby was then dried in air overnight at 120° C. and calcined in air at 450° C. for 2 hours.

The oxide catalyst C prepared thereby contained 9% by weight of the element nickel supported on alumina.

Example 4 (Invention)

Preparation of a Catalyst D with Formula Ni/Al$_2$O$_3$ by Simultaneous Impregnation (Co-Impregnation) of β-Cyclodextrin and Nickel Nitrate in Two Successive Impregnation Steps An aqueous solution containing 3.4 g of β-cyclodextrin (SIGMA-ALDRICH, 98% pure) and 11.1 g of nickel nitrate Ni(NO$_3$)$_2$, 6H$_2$O in demineralized water was prepared to a volume which corresponded to the pore volume of said alumina support. This solution was then impregnated onto 50 g of said alumina support. The solid D1 obtained thereby was then dried in air overnight at 120° C. and calcined in air at 450° C. for 2 hours.

An aqueous solution containing 3.0 g of β-cyclodextrin (SIGMA-ALDRICH, 98% pure) and 11.2 g of nickel nitrate Ni(NO$_3$)$_2$, 6H$_2$O in demineralized water was prepared to a volume which corresponded to the pore volume of the solid D1. This solution was then impregnated onto 50 g of the prepared solid D1. The solid was then dried in air overnight at 120° C. and calcined in air at 450° C. for 2 hours.

The oxide catalyst D prepared thereby contained 9% by weight of the element nickel supported on alumina.

Example 5

Passivation of Catalysts A, B, C and D in the Presence of Diethanol Disulphide

Each of catalysts A, B, C and D was passivated by sulphur using the method described in U.S. Pat. No. 5,153,163.

In order to passivate each of the catalysts, the following was carried out: a volume of 33 ml of an aqueous solution containing 0.85 g of diethanol disulphide (DEODS) and 5.1 g of formic acid was impregnated in succession onto 50 g of each of catalysts A, B, C and D. Each of the catalysts then underwent a heat treatment at 150° C. for 1 hour. Catalysts A', B', C' and D' were obtained respectively from catalysts A, B, C and D. Each of catalysts A', B', C' and D' contained 9% by weight of the element Ni and 0.7% by weight of sulphur. The catalysts A', B', C' and D' were partially in the oxide form, partially in the sulphide form and partially in the reduced form.

Example 6

Evaluation of Catalytic Properties of catalysts A', B', C' and D' in the Selective Hydrogenation of a Mixture Comprising Styrene and Isoprene in the Presence of Sulphur Before being tested in succession in the selective hydrogenation of a styrene-isoprene mixture, each of catalysts A', B', C' and D' was reduced ex situ in a stream of 1 liter of hydrogen per hour and per gram of catalyst with a temperature rise of 1° C./min and a constant temperature stage at 300° C. for 16 hours.

The selective hydrogenation reaction was carried out in a closed continuously stirred reactor, said reactor having been provided with catalyst beads, which had been transferred in the absence of air from the reactor where reduction had taken place to the closed continuously stirred reactor.

The composition of the feed to be selectively hydrogenated was as follows: 8% by weight of styrene, 8% by weight of isoprene, 10 ppm of sulphur introduced in the form of pentanethiol, 100 ppm of sulphur introduced in the form of thiophene, the solvent being n-heptane.

The selective hydrogenation reaction was carried out in the liquid phase.

The test was carried out at a constant pressure of 3.5 MPa of hydrogen and at a temperature of 60° C. The hydrogen consumption was monitored over time by the pressure drop in a reservoir bottle located upstream of the reactor.

The catalytic activities reported in Table 1 are expressed in moles of H$_2$ consumed per minute and per gram of the element nickel.

TABLE 1

Catalytic activities measured for hydrogenation of a styrene-isoprene mixture in the presence of sulphur

| Catalyst | Activity* |
|---|---|
| Catalyst A' | $3.4 \times 10^{-3}$ |
| Catalyst B' | $3.8 \times 10^{-3}$ |
| Catalyst C' | $4.3 \times 10^{-3}$ |
| Catalyst D' | $3.8 \times 10^{-3}$ |

*in (moles H$_2$)/[min × (grams of element nickel)]

The results shown in Table 1 demonstrate that catalysts B', C' and D' prepared in the presence of β-cyclodextrin are more active than the catalyst A' prepared in the absence of β-cyclodextrin. The introduction of β-cyclodextrin onto catalysts B', C' and D', irrespective of the mode of introduction, results in a gain in catalytic activity of 10% to 30%, depending on the mode or introduction, over catalyst A'.

The invention claimed is:

1. A process for the selective hydrogenation of a hydrocarbon feed comprising at least 2 carbon atoms per molecule and having an end boiling point of 250° C. or less, said hydrocarbon feed comprising acetylenes, diolefins or a mixture thereof, said process comprising bringing said feed into contact with at least one catalyst the active phase of which comprises at least one metal from group VIII deposited on a support formed by at least one oxide, said catalyst being prepared using a process comprising at least:
    i) at least once contacting said support with at least one solution containing at least one precursor of at least said metal from group VIII;

ii) at least once contacting at least said support with at least one organic compound formed from at least one cyclic oligosaccharide having at least 6 α-(1,4)-bonded glucopyranose subunits;

iii) calcining at least once to obtain at least said metal from said group VIII in the oxide form;

i) and ii) being carried out separately, in any order, or simultaneously.

2. The selective hydrogenation process according to claim 1, in which said hydrocarbon feed is a C2 steam cracked cut, a C3 steam cracked cut, a C4 steam cracked cut, a C5 steam cracked cut or a steam cracked gasoline.

3. The selective hydrogenation process according to claim 2, in which said hydrocarbon feed is a steam cracked gasoline.

4. The selective hydrogenation process according to claim 3, carried out at a temperature of 20° C. to 200° C., at a pressure of 0.4 to 5 MPa and at an hourly space velocity (defined as the ratio of the volume flow rate of feed to the volume of catalyst) of 0.2 to 30 $h^{-1}$.

5. The selective hydrogenation process according to claim 1, in which said metal from group VIII present in the active phase is nickel.

6. The selective hydrogenation process according to claim 1, in which said active phase comprises at least one additional metal from group VIII or group IB.

7. The selective hydrogenation process according to claim 1, in which said support comprises an alumina, silicas or silica alumina.

8. The selective hydrogenation process according to claim 1, in which said organic compound is a cyclodextrin, substituted cyclodextrin, polymerized cyclodextrin or a mixture of cyclodextrins.

9. The selective hydrogenation process according to claim 8, in which the cyclodextrin is α-cyclodextrin, β-cyclodextrin and γ-cyclodextrin respectively composed of 6, 7 and 8 α-(1,4)-bonded glucopyranose subunits.

10. The selective hydrogenation process according to claim 8, in which the substituted cyclodextrins is hydroxypropyl beta-cyclodextrin or methylated beta-cyclodextrins.

11. The selective hydrogenation process according to claim 1, in which said organic compound for carrying out said step ii) is introduced such that the molar ratio {(metal(s) from group VIII in the oxide form present in the active phase of the catalyst obtained from said step iii)/organic compound} is 10 to 300.

12. The selective hydrogenation process according to claim 1, in which i) and ii) are carried out simultaneously a plurality of times.

13. The selective hydrogenation process according to claim 1, in which ii) is carried out prior to i).

14. The selective hydrogenation process according to claim 1 in which, when the active phase of the catalyst comprises nickel as the metal from group VIII, said catalyst is prepared in accordance with a process comprising at least v) passivating said catalyst using at least one sulphur-containing compound.

* * * * *